United States Patent
Zhang et al.

(10) Patent No.: US 12,298,133 B2
(45) Date of Patent: May 13, 2025

(54) HIGH-RESOLUTION HANDHELD OCT IMAGING SYSTEM

(71) Applicant: THE FIRST AFFILIATED HOSPITAL OF JINAN UNIVERSITY (GUANGZHOU OVERSEAS CHINESE, Guangdong (CN)

(72) Inventors: Shuixing Zhang, Guangdong (CN); Wei Li, Guangdong (CN); Jie Tian, Guangdong (CN); Lin Yin, Guangdong (CN); Zhiyun Yang, Guangdong (CN)

( * ) Notice: Subject to any disclaimer, the term of this patent is extended or adjusted under 35 U.S.C. 154(b) by 271 days.

(21) Appl. No.: 18/149,315

(22) Filed: Jan. 3, 2023

(65) Prior Publication Data

US 2024/0133674 A1 Apr. 25, 2024
US 2024/0230315 A9 Jul. 11, 2024

(30) Foreign Application Priority Data

Oct. 24, 2022 (CN) .......................... 202211298869.X

(51) Int. Cl.
*G01B 9/02* (2022.01)
*A61B 5/00* (2006.01)
(Continued)

(52) U.S. Cl.
CPC ..... *G01B 9/02054* (2013.01); *G01B 9/02012* (2013.01); *G01B 9/02091* (2013.01);
(Continued)

(58) Field of Classification Search
CPC ............ G01B 9/02091; G01B 9/02054; G01B 9/02012; G01B 11/06; G02B 6/4202;
(Continued)

(56) References Cited

U.S. PATENT DOCUMENTS 10,222,563 B2 * 3/2019 Haase .................. G02B 6/4204
2005/0254058 A1 * 11/2005 Alphonse ........... A61B 5/14532
356/479

(Continued)

FOREIGN PATENT DOCUMENTS

CN 115192188 A * 10/2022 ............. A61B 18/20
WO WO-2015094811 A1 * 6/2015 ........... G02B 6/3882

OTHER PUBLICATIONS

Translated 1930 Czerny-Turner article (Year: 1930).*
(Continued)

*Primary Examiner* — Tarifur R Chowdhury
*Assistant Examiner* — Akbar H. Rizvi

(57) ABSTRACT

A high-resolution handheld OCT imaging system related to the optical imaging field solves the issues of handheld OCT systems with low resolution and the inability to measure the skin's stratum corneum thickness accurately. Through adopting the visible wavelength band of supercontinuum laser as the light source, mainly applying reflectors instead of lenses in the OCT system, and replacing fiber propagation with optical propagation in free space in the interference optical paths, to significantly reduce dispersion loss in the axial resolution and improve the axial resolution of OCT systems. The filter, attenuator, grating, camera, and other components are separated from the handheld module through modular design to reduce the handheld terminal's size and weight and realize the system construction. The invention improves the axial resolution, obtains the thickness information of whole-body skin's stratum corneum, and provides technical approaches for skin diagnosis and related medicine development.

10 Claims, 1 Drawing Sheet

(51) Int. Cl.
- G01B 9/02001 (2022.01)
- G01B 9/02091 (2022.01)
- G01B 11/06 (2006.01)
- G02B 6/42 (2006.01)
- G02B 17/08 (2006.01)
- G02B 26/08 (2006.01)
- G02B 26/10 (2006.01)
- G02B 27/30 (2006.01)
- H04N 23/56 (2023.01)

(52) U.S. Cl.
CPC ............ G01B 11/06 (2013.01); G02B 6/4202 (2013.01); G02B 6/4214 (2013.01); G02B 17/0832 (2013.01); G02B 26/0833 (2013.01); G02B 26/101 (2013.01); G02B 27/30 (2013.01); H04N 23/56 (2023.01); *A61B 5/0066* (2013.01)

(58) Field of Classification Search
CPC .............. G02B 6/4214; G02B 17/0832; G02B 26/0833; G02B 26/101; G02B 27/30; A61B 5/0066; A61B 5/441; H04N 23/56
See application file for complete search history.

(56) References Cited

U.S. PATENT DOCUMENTS

2014/0002907 A1* 1/2014 Liu .................... G02B 17/0868
359/641
2016/0320568 A1* 11/2016 Haase .................. G02B 6/3829

OTHER PUBLICATIONS

OCT system with a camera (Year: 2009).*
Leica OCT catalog (Year: 2010).*
Jung et al. reference (Year: 2011).*
Wikipedia on the liquid crystal dynamic range (Year: 2011).*
Liu et al. reference (Year: 2012).*
Thorlabs silvered mirrors (Year: 2012).*
Thorlabs scanner reference (Year: 2016).*
Stellarnet C-T spectrometer (Year: 2017).*
Wasatch Labs reference. (Year: 2021).*

* cited by examiner

HIGH-RESOLUTION HANDHELD OCT IMAGING SYSTEM

1. TECHNICAL FIELD

The invention relates to the field of optical imaging, in particular to a high-resolution handheld OCT imaging system.

2. BACKGROUND ART

Atopic dermatitis (AD) is a chronic recurrent inflammatory skin disease with one of the highest incidences in the world, and it is widely believed to be caused by a deficiency in the skin's stratum corneum barrier. The thickness of the stratum corneum determines the absorption rate of topical treatments for AD with a possible correlation to the barrier function preventing allergen penetration. However, existing skin testing methods, including dermoscopy, reflectance confocal microscopy, conventional optical coherence tomography (OCT), and ultrasonography, cannot accurately measure the stratum corneum's thickness in vivo, leading to the hindrance of research into precise diagnostic and therapeutic approaches for AD.

OCT is an imaging technique for in vivo 3-D visualization of tissue microstructure.

The common OCT has an axial resolution of approximately 10 μm, whereas the thickness of the stratum corneum of non-handed skin is typically 10 μm to 20 μm, and thus the axial resolution of general OCT is insufficient to accurately measure the thickness of the stratum corneum of the skin. By further improving the axial resolution of OCT and changing the high-resolution OCT system to the handheld type, it is expected to achieve accurate measurement of the thickness of the whole-body stratum corneum.

The axial resolution of OCT is related to the wavelength and frequency width of the light source. The axial resolution of OCT can be significantly improved by using a broad-spectrum light source in the visible band of a supercontinuum laser. Although some researchers have tried to construct OCT systems by using such light sources, there are still some technical problems: (1) the application of light sources in such bands is prone to significant dispersion phenomena, resulting in loss of axial resolution, making it impossible to meet the requirements for accurate measurement of the thickness of the stratum corneum; (2) while reducing the effect of dispersion and improving the axial resolution, the system probe cannot move freely and cannot be handheld, making it impossible to measure the thickness of the stratum corneum in various parts of the patient.

3. SUMMARY OF THE INVENTION

The invention provides a high-resolution handheld OCT imaging system to solve the above problems in the prior arts.

The technical solution is as follows: A high-resolution handheld OCT imaging system, wherein the system comprises a light source, optical fibers, a light source modulation module, a handheld module and an optical detection module; the light source is provided for emitting a broad-spectrum supercontinuum laser, and the light emitted from light source is connected to the light source modulation module through the first optical fiber; the light source modulation module is provided for retaining the sectional visible band of the emitted light and filtering the rest of the band and attenuating the energy of the retained light to the design value; the output light of the light source modulation module is connected to the handheld module via the second optical fiber; the handheld module is provided for the implementing optical interference in the OCT system and the scanning of the imaging target; the output light from the handheld module enters into the optical detection module via the third optical fiber; the light detection module is provided for receiving and detecting the interference light outputted by the handheld module.

Preferably, the light source modulation module comprises a first off-axis parabolic reflector, a plain glass, a beam dump, a lowpass filter, a highpass filter, a first optical-attenuating filter and a second off-axis parabolic reflector; the first off-axis parabolic reflector is provided for collimating the output light of the first optical fiber, with a small portion of the collimated light being reflected by the plain glass; the reflected light is provided for imaging and the rest of the light beam passes through the plain glass into the beam dump, to realize the safe attenuation (safe attenuation: attenuation level compatible with the system's intended operation and use) of the most of the excess light energy; the reflected light from the plain glass passed through the lowpass filter and the highpass filter is provided respectively for filtering beams with too high and too low frequencies; the light then passes through the first optical-attenuating filter for precisely attenuating the light energy to the design value; the second off-axis parabolic reflector is provided for coupling the attenuated beam into the second optical fiber.

Preferably, the handheld module comprises a third off-axis parabolic reflector, a polarizer, a beam splitter, a dispersion compensator, a second optical-attenuating filter, a first plane reflector, a two-dimensional scanning galvanometer, a second plane reflector, an objective and a fourth off-axis parabolic reflector; the third off-axis parabolic reflector is provided for collimating the output light of the second optical fiber; the collimated output light passes through the polarizer, and the polarizer is provided for changing the light beam into linearly polarized light; the linearly polarized light reaches the beam splitter and is respectively divided by the beam splitter into two beams of a first splitting-beam and a second splitting-beam; the first splitting-beam is provided as a light source for the reference arm, passing successively through the dispersion compensator and the second optical-attenuating filter; the dispersion compensator is provided for compensating for the dispersion of the objective and the second optical-attenuating filter is provided for attenuating and adjusting the light intensity in the reference arm; the output light of the second optical-attenuating filter is reflected by the first plane reflector and returned in the original path; the second splitting-beam is provided as a light source for the sample arm to reach the two-dimensional scanning galvanometer, and the two-dimensional scanning galvanometer is provided for reflecting the second splitting-beam to the second plane reflector to achieve the two-dimensional scanning of light over the sample by vibration; the second plane reflector is provided for reflecting the second splitting-beam, to enable the second splitting-beam to be directed perpendicularly into the aperture of the objective, and the objective is provided to focus the second splitting-beam on the sample to be measured; partial second splitting-beam is backscattered by the sample to be measured and returns in the original path with carrying biological information; the first and second splitting-beam of returning in the original path meet at the beam splitter and interfere; the interference light passes through the beam splitter to the fourth off-axis parabolic reflector, and the fourth off-axis parabolic reflector is provided for coupling the interference light into the third optical fiber.

Preferably, the optical detection module comprises a fifth off-axis parabolic reflector, a grating, a third plane reflector, a concave mirror, a line-scan digital camera, and a camera connection cable; the fifth off-axis parabolic reflector is provided for collimating the output light of the third optical fiber; the collimated output light passes through the grating, and the grating is provided for dispersing the light beams of different wavelengths, and the dispersed beams are reflected by the third plane reflector to reach the concave mirror; the concave mirror is provided for focusing the dispersed beams of different wavelengths on the sensor of the line-scan digital camera by reflection; the line-scan digital camera is provided for detecting the light intensity at each wavelength and transmitting the detection information to a computer via the camera connection cable.

Preferably, the light source is a supercontinuum laser with a wavelength range of 390 nm to 2400 nm.

Preferably, the first optical fiber is a photonic crystal fiber, and the optical second fiber and the third optical fiber are single-mode optical fibers.

Preferably, all the off-axis parabolic reflectors are 90-degree off-axis parabolic reflectors.

Preferably, the plain glass is made of a flat optical window.

Preferably, the lowpass and highpass filters have cut-off frequencies of 700 nm and 500 nm, respectively.

Preferably, all the optical-attenuating filters are neutral-density filters.

Preferably, the polarizer is a Glan-Thompson calcite polarizer.

Preferably, the beam splitter is a 50:50 non-polarizing beam-splitting cube.

Preferably, the dispersion compensator is a lens specifically designed to compensate for the dispersion of the objective.

Preferably, all the plane reflectors are silver-coated.

Preferably, the two-dimensional scanning galvanometer is a two-dimensional MEMS galvanometer.

Preferably, the objective is a telecentric scanning lens.

Preferably, the grating is a transmission diffraction grating.

Preferably, the concave mirror is silver-coated with a focal length of 128 mm.

Preferably, the line-scan digital camera is a line-scan digital camera formed by CMOS monochrome sensors provided in a straight line.

Preferably, the handheld module comprises a housing, which fixes the optical components in the handheld module and provides a handle.

Compared to the prior arts, the invention has the following advantages and beneficial effects:

(1) The invention adopts a broad-spectrum light source in the visible wavelength band for OCT imaging and a new optical path design to significantly reduce the loss of dispersion on the axial resolution of OCT and improve the axial resolution of the OCT system. Since the magnitude of the axial resolution of OCT is positively correlated with the central wavelength of the light source and negatively correlated with the spectral range, applying a broad-spectrum light source in the visible wavelength band can significantly improve the axial resolution of the OCT system. However, using such a light source is prone to dispersion phenomena and results in the loss of axial resolution. In the optical path design provided by the invention, the lenses leading to dispersion phenomena, including focusing lenses and lens-type collimators and couplers in conventional OCT systems, are replaced with concave mirrors, including off-axis parabolic reflectors. The design also avoids the application of optical fibers in the reference and sample arms, thus partially eliminating the loss of axial resolution due to fiber dispersion.

(2) The invention adopts a separated modular design, in which components for modulating the energy and wavelength of the light source, such as lowpass filter sheets, highpass filters, and attenuators, and components for detecting optical signals such as gratings, concave mirrors, and the line-scan digital camera, are provided in separate modules, and the construction of the OCT reference arm and sample arm is realized at the handheld terminal of the system through a compact mechanical design; and to realize a high-resolution handheld OCT imaging system through the reduction of the size and weight of the handheld terminal of the system without loss of resolution.

4. BRIEF DESCRIPTION OF ACCOMPANY DRAWINGS

In the figures, 001. the light source; 002. the first optical fiber; 003. the light source modulation module; 004. the first off-axis parabolic reflector; 005. the plain glass; 006. the beam dump; 007. the lowpass filter; 008. the highpass filter; 009. the first optical-attenuating filter; 010. the second off-axis parabolic reflector; 011. the second optical fiber; 012. the handheld module 013. the third off-axis parabolic reflector; 014. the polarizer; 015. the beam splitter; 016. the dispersion compensator; 017. the second optical-attenuating filter; 018. the first plane reflector; 019. the two-dimensional scanning galvanometer; 020. the second plane reflector; 021. the objective; 022. the sample to be measured; 023. the fourth off-axis parabolic reflector; 024. the third optical fiber; 025. the optical detection module; 026. the fifth off-axis parabolic reflector; 027. the grating; 028. the third plane reflector; 029. the concave mirror; 030. the line-scan digital camera; 031. the camera connection cable.

5. SPECIFIC EMBODIMENT OF THE INVENTION

A further description of the invention is given below in combination with the attached drawings and embodiments.

Figure 1:
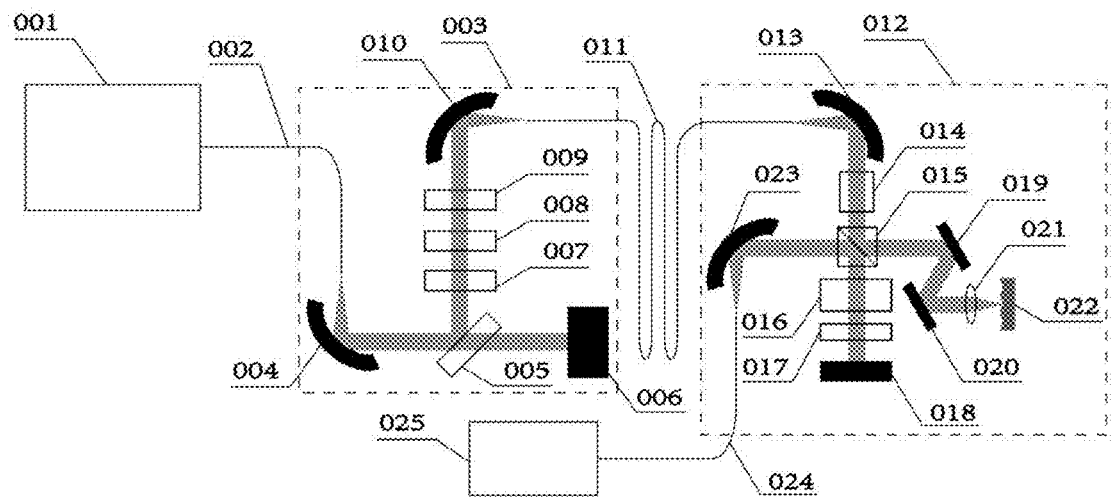
FIG. 1 is a schematic diagram showing the specific implementation of a high-resolution handheld OCT imaging system.
Figure 2:
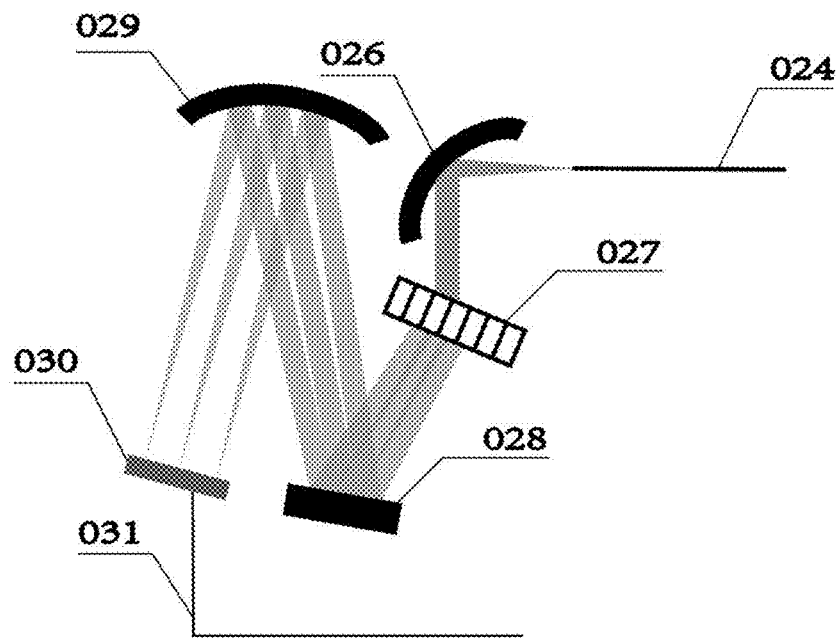
FIG. 2 is a schematic diagram showing a specific implementation of the optical detection module of a high-resolution handheld OCT imaging system.

Referring to FIG. 1, the high-resolution handheld OCT imaging system comprises a light source 001, the first optical fiber 002, the second optical fiber 011, the third optical fiber 024, a light source modulation module 003, a handheld module 012 and an optical detection module 025.

The light source 001 is provided for emitting a broad-spectrum supercontinuum laser with a wavelength range of 390-2400 nm, and the light emitted from the light source is connected to the light source modulation module 003 through the first optical fiber 002.

The light source 001 adopts the FIU-6 OCT supercontinuum laser light source from NKT Photonics.

The first optical fiber 002 adopts the LMA-5 output single-mode photonic crystal fiber from NKT Photonics.

The light source modulation module 003 comprises a first off-axis parabolic reflector 004, a plain glass 005, a beam dump 006, a lowpass filter 007, a highpass filter 008, a first optical-attenuating filter 009 and a second off-axis parabolic reflector 010; the first off-axis parabolic reflector 004 is provided for collimating the output light of the first optical fiber 002, and the collimated beam reaches the flat glass 005 for the reflection and transmission; more than 90% of the beam undergoes transmission and reaches the beam dump 006, thus dissipating the excessive light energy safely; about 8% of the beam is reflected by the plain glass 005 and passes successively through the lowpass filter 007, the highpass filter 008 and the first optical-attenuating filter 009; the lowpass filter 007 and highpass filter 008 respectively have cut-off frequencies of 700 nm and 500 nm, thereby allowing light sources in the 500-700 nm band to pass through and light sources in other bands to be filtered out; the first optical-attenuating filter 009 provides precise light intensity attenuation of the 500-700 nm light source to the design value; the output light from the first optical-attenuating filter 009 reaches the second off-axis parabolic reflector 010, to be reflected, focused, and coupled into the second optical fiber 011.

The output light of the light source modulation module 003 is connected to the handheld module 012 via the second optical fiber 003.

The handheld module 012 comprises the third off-axis parabolic reflector 013, the polarizer 014, the beam splitter 015, the dispersion compensator 016, the second optical-attenuating filter 017, the first plane reflector 018, the two-dimensional scanning galvanometer 019, the second plane reflector 020, the objective 021 and the fourth off-axis parabolic reflector 023; the third off-axis parabolic reflector 013 is provided for collimating the output light of the second optical fiber 011; the collimated output light passes through the polarizer 014 to be changed into linearly polarized light; the linearly polarized light reaches the 50:50 beam splitter 015 and is respectively divided by the beam splitter 015 into two beams of the first splitting-beam and a second splitting-beam; the first splitting-beam passes through the beam splitter 015 into the reference arm and the second splitting-beam is reflected by the beam splitter 015 into the sample arm; the first splitting-beam passes successively through the dispersion compensator 016 and the second optical-attenuating filter 017; the dispersion compensator 016 is provided for compensating for the dispersion of the objective 021 to reduce the loss of resolution due to objective dispersion, and the second optical-attenuating filter 017 is provided for attenuating and adjusting the light intensity in the reference arm to achieve equal output light intensity of the reference arm and the sample arm; the first splitting-beam is reflected by the first plane reflector and returned in the original path to reach the beam splitter 015; the second splitting-beam is reflected by the two-dimensional scanning galvanometer 019 in the sample arm to reach the second plane reflector 020, to realize the scanning of the beam in the two-dimensional plane by means of the biaxial vibration of the two-dimensional scanning galvanometer 019; the second splitting-beam is reflected by the second plane reflector 020, to enable the second splitting-beam to be directed perpendicularly into the aperture of the objective 021; the objective 021 focuses the second splitting-beam on the sample to be measured 022 for biological information detection; partial second splitting-beam is backscattered by the sample to be measured 022 and returns in the original path with carrying biological information; the first and second splitting-beam of returning in the original path meet at the beam splitter 015 with respectively occurring reflection and transmission 015 to be combined into one beam, and interfere to reach the fourth off-axis parabolic reflector 023; the fourth off-axis parabolic reflector 023 couples the interference light into the third optical fiber 024 by reflection.

The handheld module 012 comprises a housing to fix the optical components in the handheld module and provides a handle to realize the convenient handheld inspection; to ensure the lightness and reliability of the housing, the housing is formed and processed by a 3-D printing method.

The polarizer 014 is a Glan-Thompson calcite polarizer GTH5M from Thorlabs.

The beam splitter 015 is a 50:50 non-polarizing beam-splitting cube BS010 from Thorlabs.

The objective 021 and dispersion compensator 016 is a 400-700 nm telecentric scanning lens LSM03-VIS from Thorlabs, and a matching dispersion compensator LSM03DC-VIS, respectively.

The two-dimensional scanning galvanometer is a two-dimensional MEMS galvanometer A8L2.2-5000AL from Mirrorcle Technologie.

The output light from the handheld module 012 enters the optical detection module 025 through the third optical fiber 024; the second optical fiber 011 and the third optical fiber 024 adopt the special fiber RGB400 from Corning.

The optical detection module 025 comprises the fifth off-axis parabolic reflector 026, the grating 027, the third plane reflector 028, the concave mirror 029, the line-scan digital camera 030 and the camera connection cable 031; the fifth off-axis parabolic reflector 026 reflects and collimates the output light of the third optical fiber 024 to be guided to the transmission grating 027; the grating 027 disperses the light beams of different wavelengths to be guided to the third plane reflector 028; the dispersed beams of different wavelengths is reflected by the third plane reflector 028 to reach the concave mirror 029; the concave mirror 029 focuses the dispersed beams of different wavelengths on the sensor of the line-scan digital camera 30 by reflection; the line-scan digital camera 030 converts the focused light signal into electrical signal and transmits the electrical signal into the computer through the camera connection cable 031, to realize the image reconstruction and display through the computer.

The first off-axis parabolic reflector 004, the third off-axis parabolic reflector 013, and the fifth off-axis parabolic reflector 026 are all silver-coated reflective collimators RC02APC-P01 from Thorlabs, and the second off-axis parabolic reflector 010 and the fourth off-axis parabolic reflector 023 are both 90-degree off-axis parabolic reflectors MPD00M9-P01 from Thorlabs.

The grating 027 is a volume phase holographic grating 1000 l/mm @600 nm from Wasatch.

The concave mirror 029 is a customized silver-coated concave mirror with a focal length of 128 mm designed by Zemax.

The line-scan digital camera 030 is a line-scan digital camera e2v OCTOPLUS consisting of 2048 monochrome CMOS sensors from Teledyne e2v.

The invention significantly improves the axial resolution of the OCT system by optical design, including using reflectors instead of transmission mirrors, avoiding the application of optical fibers in the optical interference optical path, and partially preventing the loss of axial resolution caused by the dispersion of lenses and optical fibers in the conventional OCT system. In addition, through the modular design of the system and the compact arrangement of the handheld terminal, the size and weight of the handheld end are reduced without loss of resolution to realize the construction of a high-resolution handheld OCT imaging system.

The principle of the imaging technique provided in the invention is the same as that of conventional spectral domain optical coherence tomography (SD-OCT). In the imaging system provided by the invention, the broadband laser light source is divided into two beams: one beam is guided onto the tissue to be measured and backscattered on internal structures of the tissue at different depths to become the signal light; the other beam is reflected on the reference mirror in a fixed position to become the reference light. The system adopts a device similar to the spectrometer to measure the interference fringe of these two beams, the spatial frequency of which is a function of the difference in optical range between the signal light and the reference light, and the difference in optical range is related to the depth of the tissue structure. Thus, signal light at different tissue depths will produce different frequency modulations. It is possible to obtain individual frequency components of the interferometric fringe signal through Fourier transformation, and the frequency of the signal and the intensity of the component represent the depth and amplitude of the signal light of the tissue, respectively, to form a set of axial scanning data. Two-dimensional or three-dimensional imaging of the tissue can be achieved by scanning the beam over the tissue and image reconstruction.

The embodiments of the invention are disclosed and described hereinabove. Any transformation and modification of the structural methods and embodiments similar to the technical solution without departing from the inventive purpose of the invention made by inspired ordinary technicians in the art without creative efforts shall all fall within the protection scope of the invention. The scope of the invention should be determined with reference to the appended claims, along with the full scope of equivalents to which such claims are entitled.

The invention claimed is:

1. A high-resolution handheld OCT imaging system, wherein the system comprises a light source, optical fibers, a light source modulation module, a handheld module, and an optical detection module;
the light source is provided for emitting a broad-spectrum supercontinuum laser light, and a light is emitted from the light source, the light source is connected to the light source modulation module through a first optical fiber;
the light source modulation module is provided for retaining the emitted light in the visible band and filtering the rest of the band, and attenuating an energy of the retained light to a design value;
the output light of the light source modulation module is connected to the handheld module via a second optical fiber;
the handheld module is provided for the implementation of optical interference in the OCT system and the scanning of an imaging target;
the output light from the handheld module enters the optical detection module via a third optical fiber;
the light detection module is provided for receiving and detecting an interference light outputted by the handheld module.

2. The high-resolution handheld OCT imaging system according to claim 1, wherein the light source modulation module comprises a first off-axis parabolic reflector, a flat glass, a beam dump, a lowpass filter, a highpass filter, a first optical-attenuating filter and a second off-axis parabolic reflector; the first off-axis parabolic reflector is provided for collimating the output light of the first optical fiber, with a fraction of the collimated light being reflected by the flat glass; the reflected light is provided for imaging and the rest of a light beam passes through the flat glass into the beam dump, to realize the safe attenuation of the most of the excess light energy; the reflected light from the flat glass passed through the lowpass filter and the highpass filter is provided respectively for filtering beams with too high and too low frequencies; the light then passes through the first optical-attenuating filter for precisely attenuating the light energy to the design value; the second off-axis parabolic reflector is provided for coupling the attenuated beam into the second optical fiber.

3. The high-resolution handheld OCT imaging system according to claim 1, wherein the handheld module comprises a third off-axis parabolic reflector, a polarizer, a beam splitter, a dispersion compensator, a second optical-attenuating filter, a first plane reflector, a two-dimensional scanning galvanometer, a second plane reflector, an objective and a fourth off-axis parabolic reflector; the third off-axis parabolic reflector is provided for collimating the output light of the second optical fiber; the collimated output light passes through the polarizer, and the polarizer is provided for changing the light beam into linearly polarized light; the linearly polarized light reaches the beam splitter and is respectively divided by the beam splitter into two beams of a first splitting-beam and a second splitting-beam; the first splitting-beam is provided as a light source for the reference arm, passing successively through the dispersion compensator and the second optical-attenuating filter; the dispersion compensator is provided for compensating for the dispersion of the objective and the second optical-attenuating filter is provided for attenuating and adjusting a light intensity in a reference arm; the output light of the second optical-attenuating filter is reflected by the first plane reflector and reflected back; the second splitting-beam is provided as a light source for a sample arm to reach the two-dimensional scanning galvanometer, and the two-dimensional scanning galvanometer is provided for reflecting the second splitting-beam to the second plane reflector to achieve the two-dimensional scanning of light over a sample by vibration; the second plane reflector is provided for reflecting the second splitting-beam, to enable the second splitting-beam to be directed into the aperture of the objective, and the objective is provided to focus the second splitting-beam on the sample to be measured; the second splitting-beam is backscattered by the sample to be measured and propagated back with carrying biological information; the first and second splitting-beam of returning in the original path meet at the beam splitter and interfere; the interference light passes through the beam splitter to the fourth off-axis parabolic reflector, and the fourth off-axis parabolic reflector is provided for coupling the interference light into the third optical fiber.

4. The high-resolution handheld OCT imaging system according to claim 1, wherein the optical detection module comprises a fifth off-axis parabolic reflector, a grating, a third plane reflector, a concave mirror, a line-scan digital camera, and a camera connection cable; the fifth off-axis parabolic reflector is provided for collimating the output light of the third optical fiber; the collimated output light passes through the grating, and the grating is provided for dispersing the light beams of different wavelengths, and the dispersed beams are reflected by the third plane reflector to reach the concave mirror; the concave mirror is provided for focusing the dispersed beams of different wavelengths on a sensor of the line-scan digital camera by reflection; the line-scan digital camera is provided for detecting the light intensity at each wavelength and transmitting the detection information to a computer via the camera connection cable.

5. The high-resolution handheld OCT imaging system according to claim 1, wherein the first optical fiber is a photonic crystal fiber, and the second optical fiber and the third optical fiber are single-mode optical fibers.

6. The high-resolution handheld OCT imaging system according to claim 3, wherein the dispersion compensator is a lens specifically designed to compensate for the dispersion of the objective.

7. The high-resolution handheld OCT imaging system according to claim 2, wherein the off-axis parabolic reflectors are 90-degree off-axis parabolic reflectors.

8. The high-resolution handheld OCT imaging system according to claim 3, wherein the two-dimensional scanning galvanometer is a two-dimensional MEMS galvanometer.

9. The high-resolution handheld OCT imaging system according to claim 4, wherein the concave mirror is a silver-coated concave mirror with a focal length of 128 mm.

10. The high-resolution handheld OCT imaging system according to claim 3, wherein the handheld module comprises a housing which fixes the optical components in the handheld module and provides a handle.

* * * * *